US010754882B2

(12) United States Patent
Gholap et al.

(10) Patent No.: US 10,754,882 B2
(45) Date of Patent: Aug. 25, 2020

(54) METHOD OF RETRIEVING INFORMATION FROM A HEALTH REPORT THROUGH A MACHINE ASSISTED INTERROGATION PROCESS

(71) Applicant: Optra Health, Inc., Cupertino, CA (US)

(72) Inventors: Abhijeet Sharadchandra Gholap, Cupertino, CA (US); Nitin Sharma, Pune (IN); Gauri Gholap, Cupertino, CA (US); Ashwin Kotwaliwale, Cupertino, CA (US)

(73) Assignee: OPTRA HEALTH, INC, Cupertino, CA (US)

( * ) Notice: Subject to any disclaimer, the term of this patent is extended or adjusted under 35 U.S.C. 154(b) by 181 days.

(21) Appl. No.: 16/170,016

(22) Filed: Oct. 24, 2018

(65) Prior Publication Data

US 2019/0121903 A1 Apr. 25, 2019

Related U.S. Application Data

(60) Provisional application No. 62/576,319, filed on Oct. 24, 2017.

(51) Int. Cl.
| | | |
|---|---|---|
| *G16H 10/60* | (2018.01) | |
| *G06F 16/24* | (2019.01) | |
| *G06F 16/33* | (2019.01) | |
| *G10L 15/18* | (2013.01) | |
| *G06F 16/31* | (2019.01) | |
| *G06F 16/338* | (2019.01) | |
| *G06F 16/332* | (2019.01) | |

(52) U.S. Cl.
CPC ......... *G06F 16/3334* (2019.01); *G06F 16/24* (2019.01); *G06F 16/313* (2019.01); *G06F 16/338* (2019.01); *G06F 16/3329* (2019.01); *G10L 15/18* (2013.01); *G16H 10/60* (2018.01)

(58) Field of Classification Search
CPC ............................... G06F 16/24; G16H 10/00
See application file for complete search history.

(56) References Cited

U.S. PATENT DOCUMENTS

| | | | | |
|---|---|---|---|---|
| 2007/0226294 A1* | 9/2007 | Pruitt | ............... | H04L 61/1541 709/203 |
| 2009/0182585 A1* | 7/2009 | Harkensee | ............ | G06Q 40/08 705/4 |
| 2010/0293090 A1* | 11/2010 | Domenikos | .......... | G06Q 40/025 705/38 |
| 2011/0161110 A1* | 6/2011 | Mault | ................... | G16H 40/67 705/3 |

(Continued)

*Primary Examiner* — Charles E Lu

(57) ABSTRACT

A method of retrieving information from a health report through a machine assisted interrogation process consists of a personal assistance device, a reporting system, a knowledge-graphing system, and a query-interrogation system. A user utilizes the personal assistance device to submit a query that retrieves information from the reporting system via the query-interrogation system. The knowledge-graphing system, which is generated using artificial intelligence modules, natural language understanding modules, and machine learning modules, is utilized to provide accurate results to the user. An administrative system monitors the validity of a plurality of health reports of the reporting system.

15 Claims, 13 Drawing Sheets

(56) References Cited

U.S. PATENT DOCUMENTS

| | | | |
|---|---|---|---|
| 2011/0208766 A1* | 8/2011 | Lang | G06Q 10/10 |
| | | | 707/759 |
| 2011/0218821 A1* | 9/2011 | Walton | G06Q 50/24 |
| | | | 705/3 |
| 2015/0039343 A1* | 2/2015 | Cline | G16H 50/30 |
| | | | 705/3 |
| 2016/0078195 A1* | 3/2016 | Sarkar | G16H 10/60 |
| | | | 705/3 |
| 2016/0162172 A1* | 6/2016 | Rathod | G06F 9/451 |
| | | | 715/747 |
| 2017/0199797 A1* | 7/2017 | Hresko | G06F 11/3013 |

* cited by examiner

METHOD OF RETRIEVING INFORMATION FROM A HEALTH REPORT THROUGH A MACHINE ASSISTED INTERROGATION PROCESS

The current application claims a priority to the U.S. Provisional Patent application Ser. No. 62/576,319 filed on Oct. 24, 2017.

FIELD OF THE INVENTION

The present invention relates generally to a method of identifying and understanding the information in a health report. More specifically, the present invention introduces a method for a user to understand a personal health report through an interrogation process.

BACKGROUND OF THE INVENTION

Generally, a health report consists of a set of healthcare related terms and numerical data that is unfamiliar to an individual not related to the healthcare field. Thus, understanding a health report requires a considerable amount of time and effort.

The lack of communication between a healthcare professional and a consumer can lead to many unfavorable circumstances. As an example, if the consumer is within a dangerous range for a specific health condition, and the consumer is unable to understand the situation by looking at the health report, the health of the consumer can be in serious risk. Therefore, the need for a method that can clearly communicate the vital information of a health report is clearly seen.

Another disadvantage of existing health report is the lack of providing relevant information. For instance, if a consumer is undergoing a certain health condition, current health reports only show the relevant data. The health report does not provide information on what resulted in a certain health condition or on what can be done to get rid of the condition.

The objective of the present invention is to address the aforementioned issues. To do so, the present invention introduces a method of interrogation that allows the user to understand the content of the health report. The present invention utilizes a set of systems and personal-computing devices that allow the user to directly interact with the present invention. Overall, the present invention intends to simplify the process of understanding a health report.

DETAIL DESCRIPTIONS OF THE INVENTION

All illustrations of the drawings are for the purpose of describing selected versions of the present invention and are not intended to limit the scope of the present invention.

The present invention introduces a method that can be used to understand the content of a health report. To do so, the present invention utilizes an interrogation method that allows the user to communicate with a personal assistance device and understand the content of a health report. By utilizing the present invention, the user can fully understand a health report and avoid any possible discrepancies.

To fulfill the intended functionalities, the present invention is provided with a reporting system that comprises a plurality of health reports and a query-interrogation system. The reporting system is preferably managed by at least one remote server. Each of the plurality of health reports contain information that can be, but is not limited to, healthcare terms and health test reports. The query-interrogation system is used to extract the required information from the plurality of health reports according to the user input. To access the plurality of health reports through an interrogation method, the present invention is provided with a personal assistance device which is communicably coupled with the reporting system. The personal assistance device can be, but is not limited to, a virtual assistance device, a personal computer or mobile phone.

As seen in FIGS. 1-3B, when the present invention is used to retrieve information, the present invention initially receives a health report-related query through the personal assistance device. The health report-related query is mapped to a specific health report of the plurality of health reports by means of a verification system. Upon receiving the health report-related query, the present invention forwards the health report-related query from the personal assistance device to the query interrogation system.

To provide the most relevant information to the health report-related query, the present invention compiles a corresponding knowledge corpus for the specific health report through a knowledge-graphing system which is preferably managed by the at least one remote server. The corresponding knowledge corpus consists of a query-related knowledge graph and a report-related knowledge graph. The query-related knowledge graph is generated according to the health report-related query. On the other hand, the report-related knowledge graph is generated from the specific health report and other sources of information which can be, but is not limited to, thesauruses, healthcare and literature databases.

Figure 9:
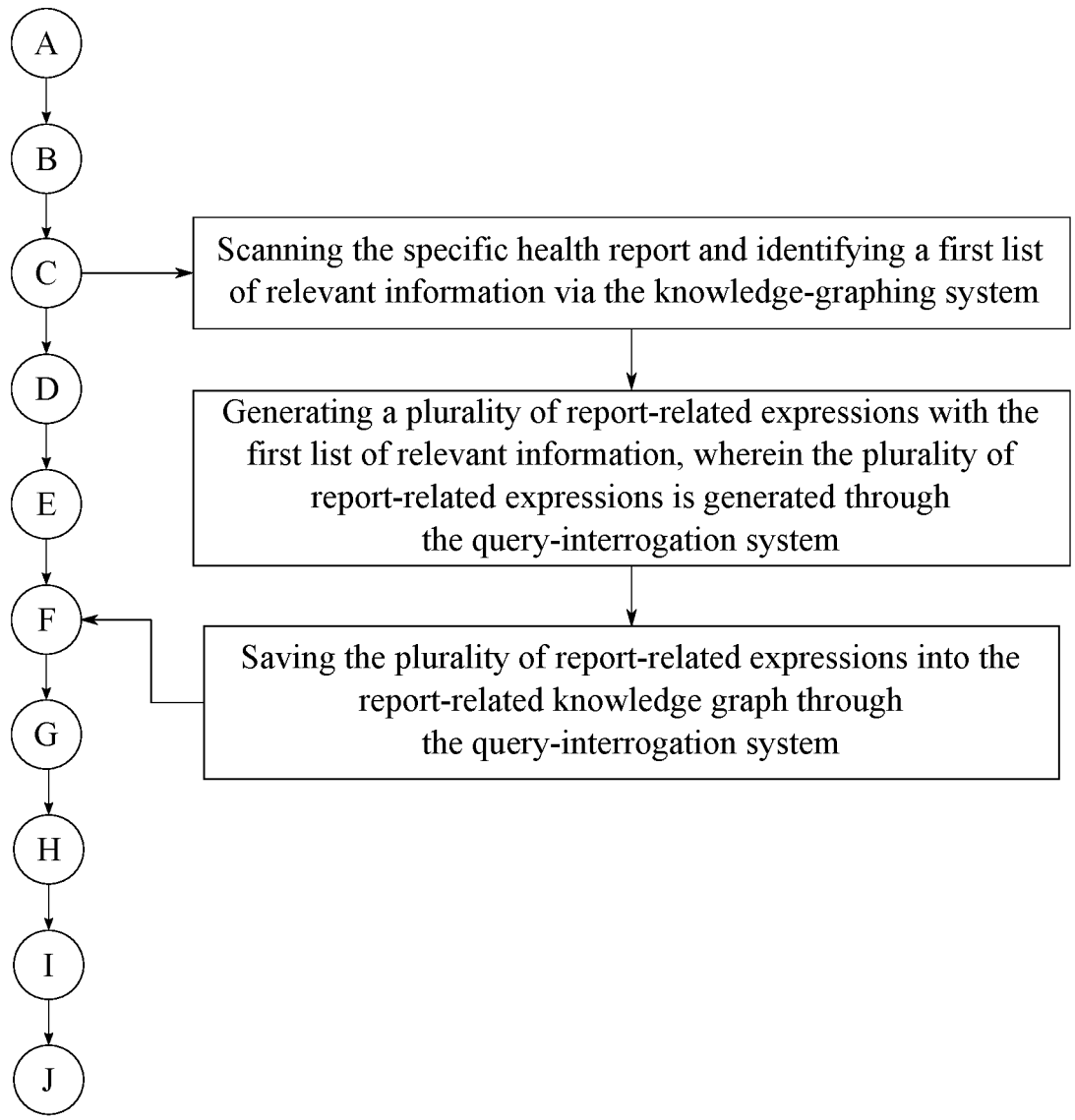
FIG. 9 is a flowchart illustrating the basic overall process of generating the report-related knowledge graph for the specific health report.

As illustrated in FIG. 9, to generate the report-related knowledge graph, the specific health report is scanned with the knowledge-graphing system to identify a first list of relevant information. The first list of relevant information can be, but is not limited to, a plurality of healthcare-related ontologies, a plurality of healthcare-related keywords and a plurality of health-related concepts. When the first list of relevant information is identified, a coreference resolution method is applied via the knowledge-graphing system to generate a plurality of report-related expressions that is then saved into the report-related knowledge graph. The plurality of report-related expressions can be, but is not limited to, a plurality of unsolved and resolved sentences. As mentioned before, the report-related knowledge-graph combines information from healthcare literature databases and other healthcare databases which are continually and programmatically acquired by the present invention. A report-related knowledge-graph is thus a collection of data from the report and related information from other data sources, organized as a graph of associations of various healthcare entities.

Figure 10:
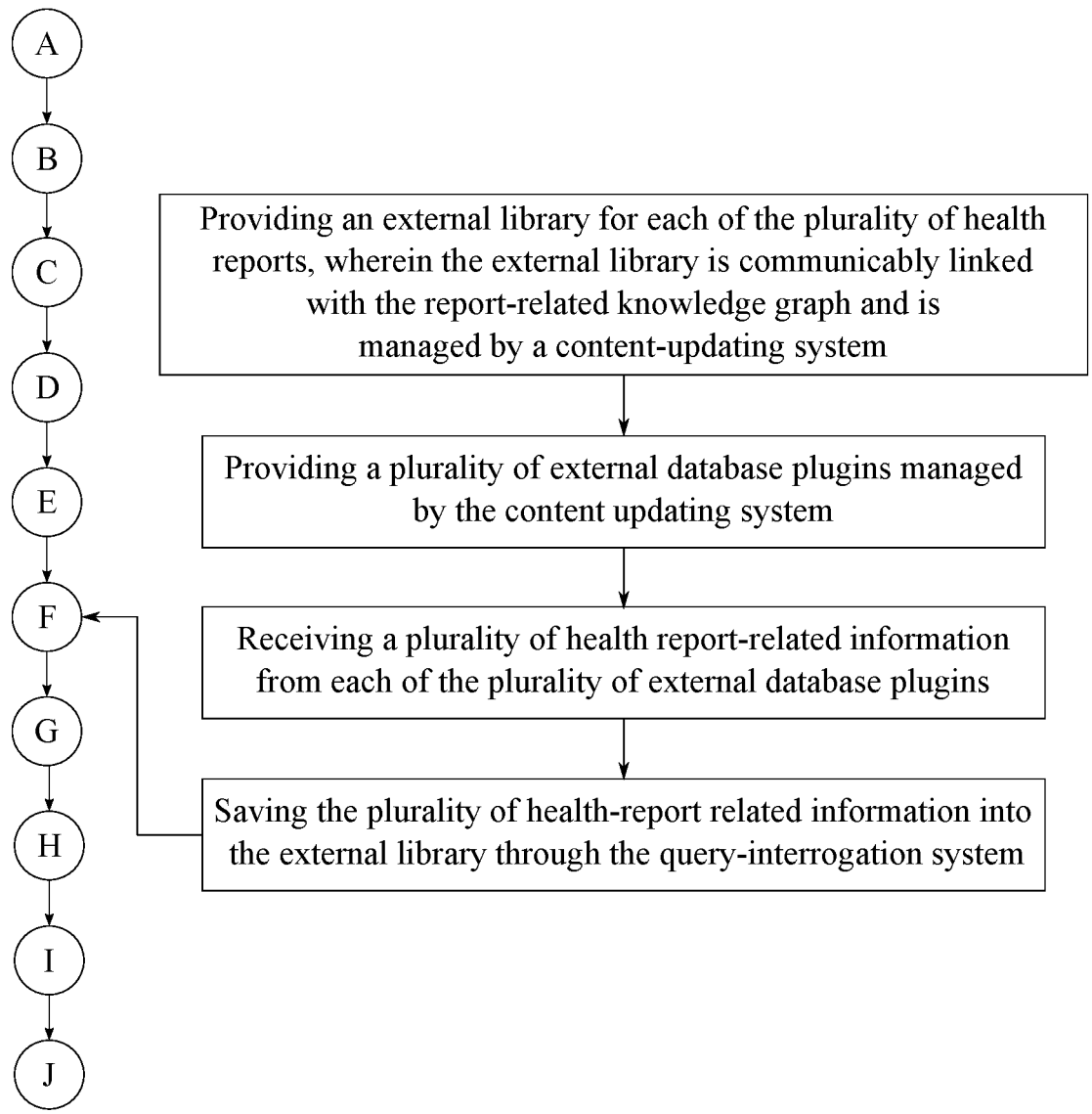
FIG. 10 is a flowchart illustrating the basic overall process of generating the report-related knowledge graph with health report-related information received from a plurality of external database plugins.

As illustrated in FIG. 10, to retrieve information from external healthcare related databases, the present invention is further provided with an external library for each of the plurality of health reports, wherein the external library is managed by a content-updating system that is a computer-executable program managed by the at least one remote server. In order to transfer information between the external library and the report-related knowledge graph of each of the plurality of health reports, the external library is communicably coupled with the report-related knowledge graph through the content-updating system. To constantly update the external library with content that can be used to generate the list of query-related information, the present invention is further provided with a plurality of external database plugins that is managed by the content-updating system. Each of the plurality of external database plugins will be distributed among various sources that can be used to retrieve information related to the field of healthcare. As discussed before, the external sources can be, but is not limited to, thesauruses and healthcare databases. The present invention receives a plurality of health report-related information from each of the plurality of external plugins which is then saved into external library through the query-interrogation system. The plurality of health report-related information can be, but is not limited to, healthcare related keyword synonyms. Thus, the report-related knowledge graph of the specific health report can be updated with the healthcare related keywords and synonyms.

Figure 11:
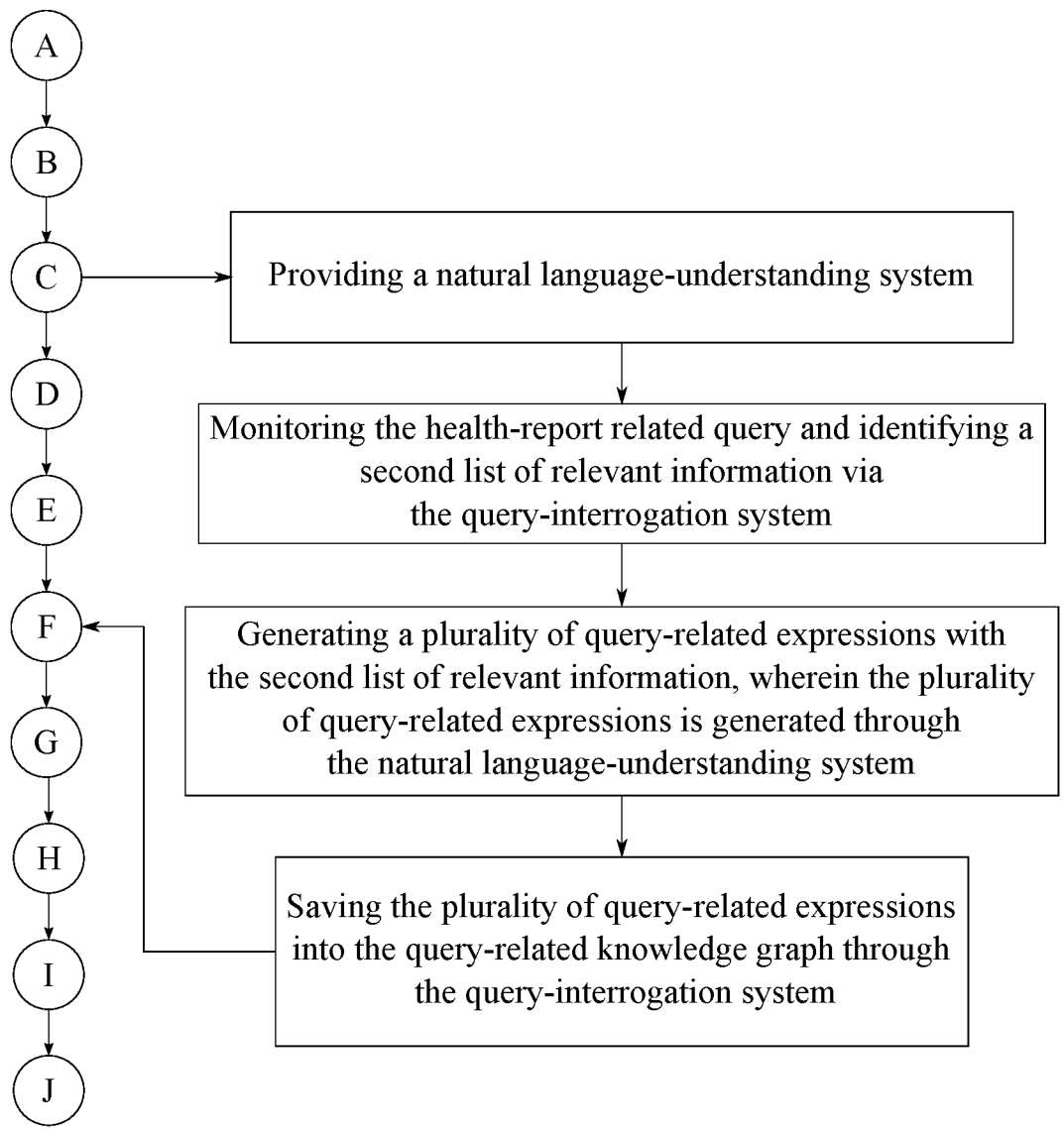
FIG. 11 is a flowchart illustrating the basic overall process of generating a query-related knowledge graph.

As illustrated in FIG. 11, to generate the query-related knowledge graph, the present invention monitors the health report-related query and identifies a second list of relevant information through the knowledge-graphing system. The second list of relevant information can be, but is not limited to, a plurality of healthcare-related ontologies and a plurality of healthcare-related keywords. When the second list of relevant information is identified, a coreference resolution method is applied via the knowledge-graphing system to generate a plurality of query-related expressions that is then saved into the query-related knowledge graph. To understand the health-report related query that was received from the user, the present invention utilizes a natural language-understanding system which is preferably managed by the at least one remote server. More specifically, the natural language-understanding system is used to identify and extract the meaning of the health-report related query. The plurality of query-related expressions can be, but is not limited to, a plurality of unsolved and resolved sentences.

Figure 12:
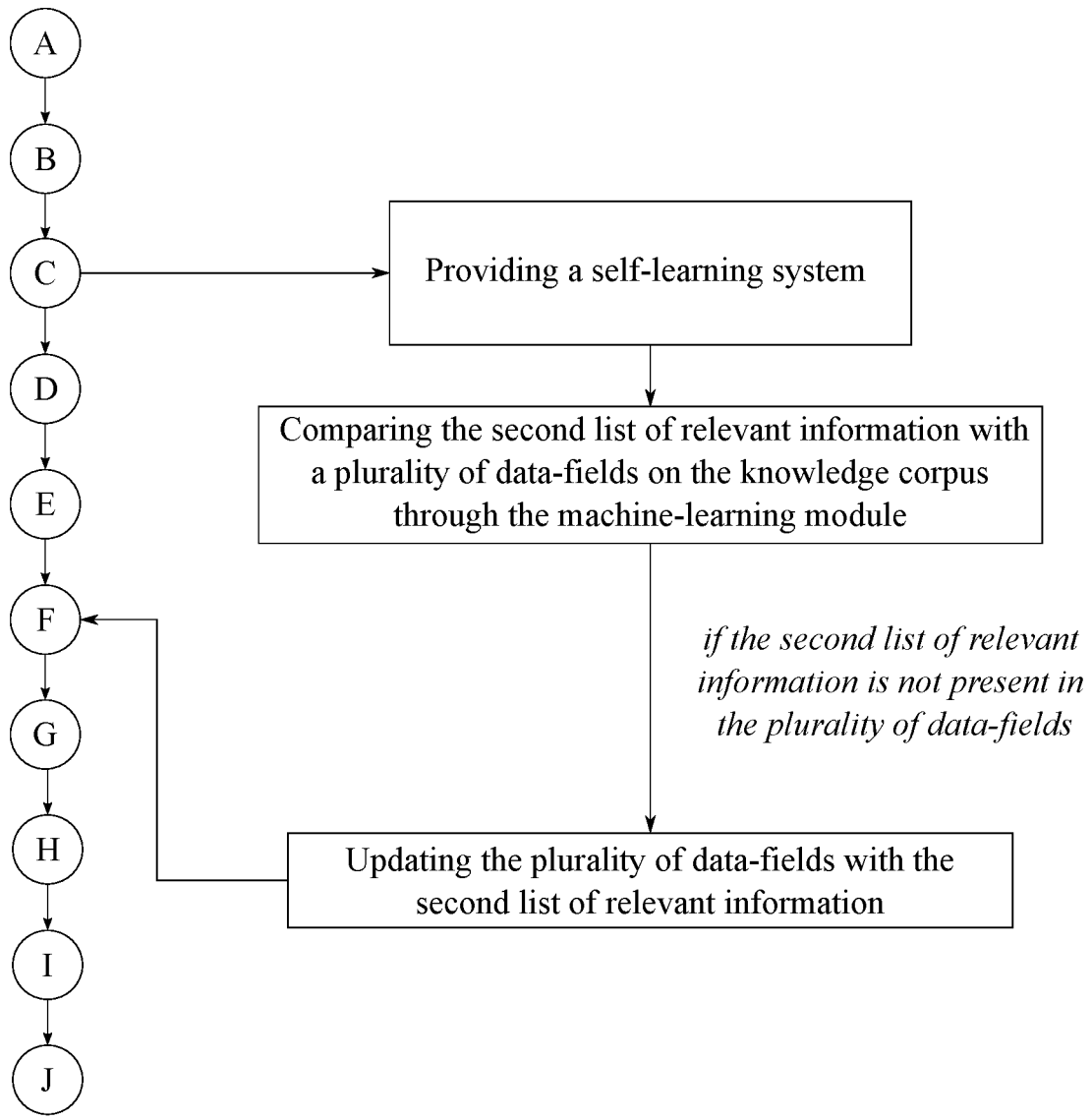
FIG. 12 is a flowchart illustrating the basic overall process of updating the query-related knowledge graph.

As illustrated in FIG. 12, the present invention also consists of a self-learning aspect that allows the present invention to update the corresponding knowledge corpus upon receiving the health report-related query. To do so, the present invention is provided with a self-learning system which is preferably managed by the at least one remote server. The present invention compares the second list of relevant information with a plurality of data-fields on the corresponding knowledge corpus through the self-learning system. After comparing the second list of relevant information, the present invention updates the plurality of data-fields with the second list of relevant information if the second list of relevant information is not present in the plurality of data-fields. The self-learning system ensures that system accuracy is continuously maintained.

The self-learning system can also be used to update the corresponding knowledge corpus with a new query and the list of query-related information that addresses the new query. More specifically, if the present invention is unable to provide an appropriate response to the new query, the present invention proceeds to respond to the new query with a first most-relevant response, a second most-relevant response, and a third most-relevant response that are generated by the query-interrogation system, wherein each of the responses is a list of query-related information. Moreover, in this instance, the relevance to the new query reduces from the first most-relevant response to the third most-relevant response. If the first most-relevant response satisfies the new query, the first most-relevant response is saved into the query-related knowledge graph as a primary response for the new query. If the second most-relevant response satisfies the health-report related query, the second most-relevant response is saved into the query-related knowledge graph as the primary response. If the third most-relevant response satisfies the health-report related query, the third most-relevant response is saved as the primary response. The first most-relevant response, the second most-relevant response or the third most-relevant response is saved onto the query-related knowledge graph through the self-learning system. Thus, the overall accuracy of the present invention is improved. Even though only the first most-relevant response, the second most-relevant response, and the third most-relevant response are described in the preferred embodiment, a plurality of most-relevant responses can be generated in other embodiments of the present invention. In such instances, each of the plurality of most-relevant responses will be ordered according to relevance.

After the specific health report is selected, the knowledge-graphing system extracts a list of query-related information from the corresponding knowledge corpus of the specific health report. To do so, the query-related knowledge graph is compared and associated with the report-related knowledge graph through the knowledge-graphing system. By doing so, the knowledge-graphing system determines a plurality of intersection points that is then used to extract the list of query-related information.

When the list of query-related information is extracted, the present invention forwards the list of query-related information from the query-interrogation system to the personal assistance device so that the user can receive an answer through the personal assistance device. In doing so, the present invention converts the list of query-related information to an output content file through the query-interrogation system which is then outputted through the personal assistance device. Thus, the output content file will contain information that is a response to the health report-related query.

The personal assistance device can vary in different embodiments of the present invention. As illustrated in FIG.

4, if the personal assistance device is intended to be activated via voice commands, the present invention is provided with a text-voice converting system managed by a command receiving system, wherein the command receiving system is a computer-executable program managed by the at least one remote server. When voice commands are utilized, the output content file will be a playable media file that is replayed through the personal assistance device.

Figure 1:
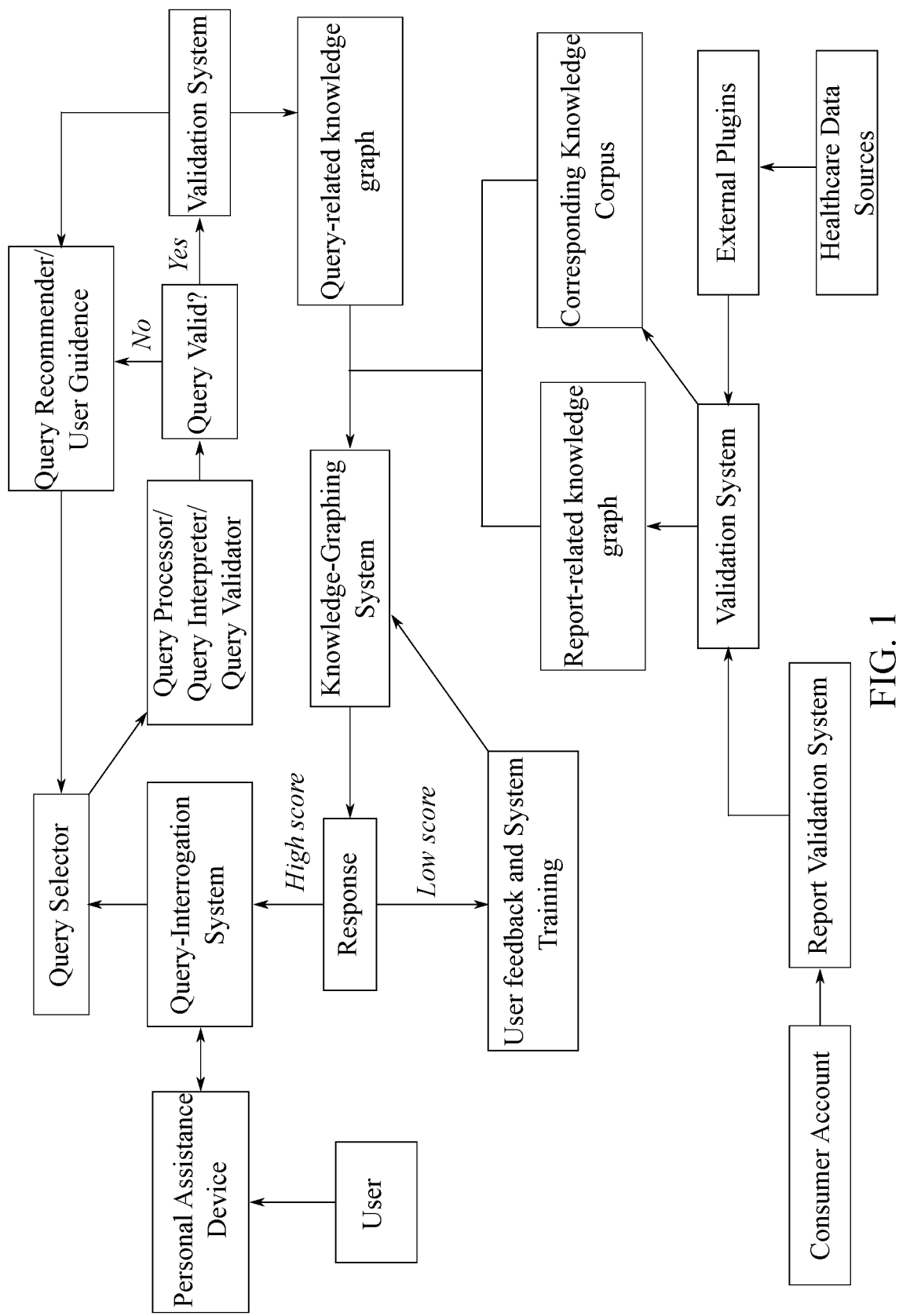
FIG. 1 is a block diagram of an exemplary embodiment of the present invention.
Figure 2:
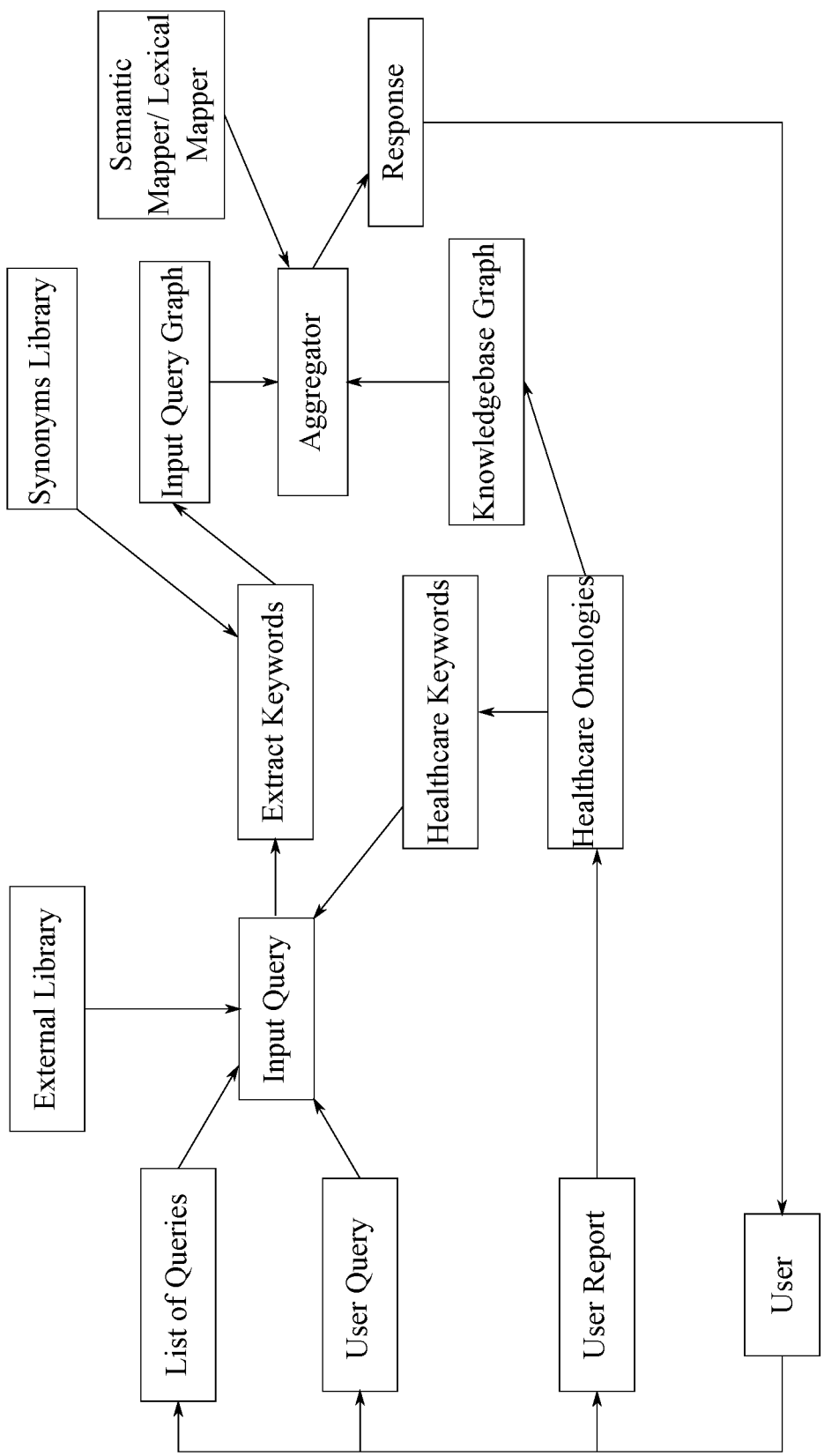
FIG. 2 is a block diagram of the process of generating a corresponding knowledge corpus in the exemplary embodiment of the present invention.
Figure 3A:
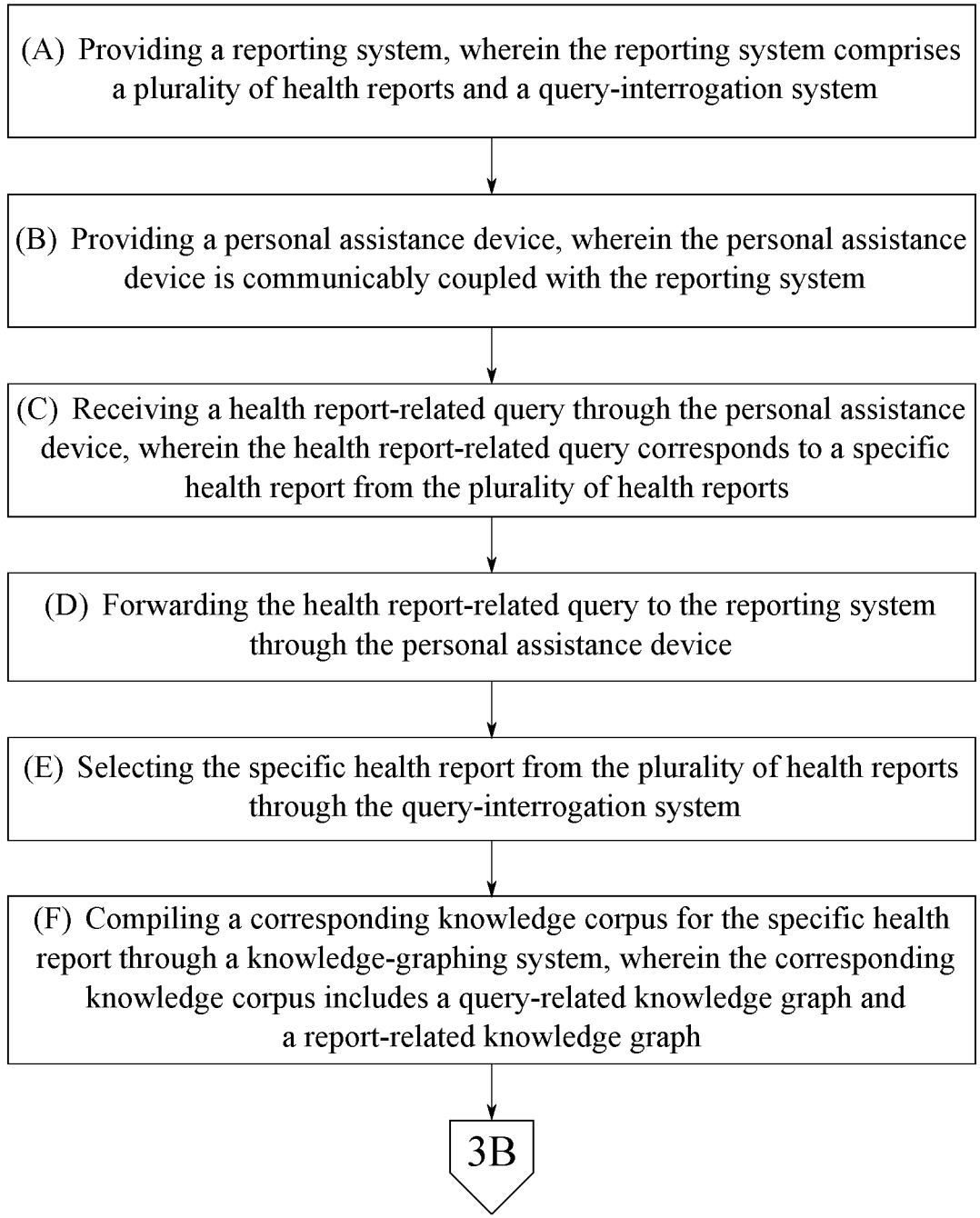
FIG. 3A is a flowchart illustrating the overall process of the present invention.
Figure 3B:
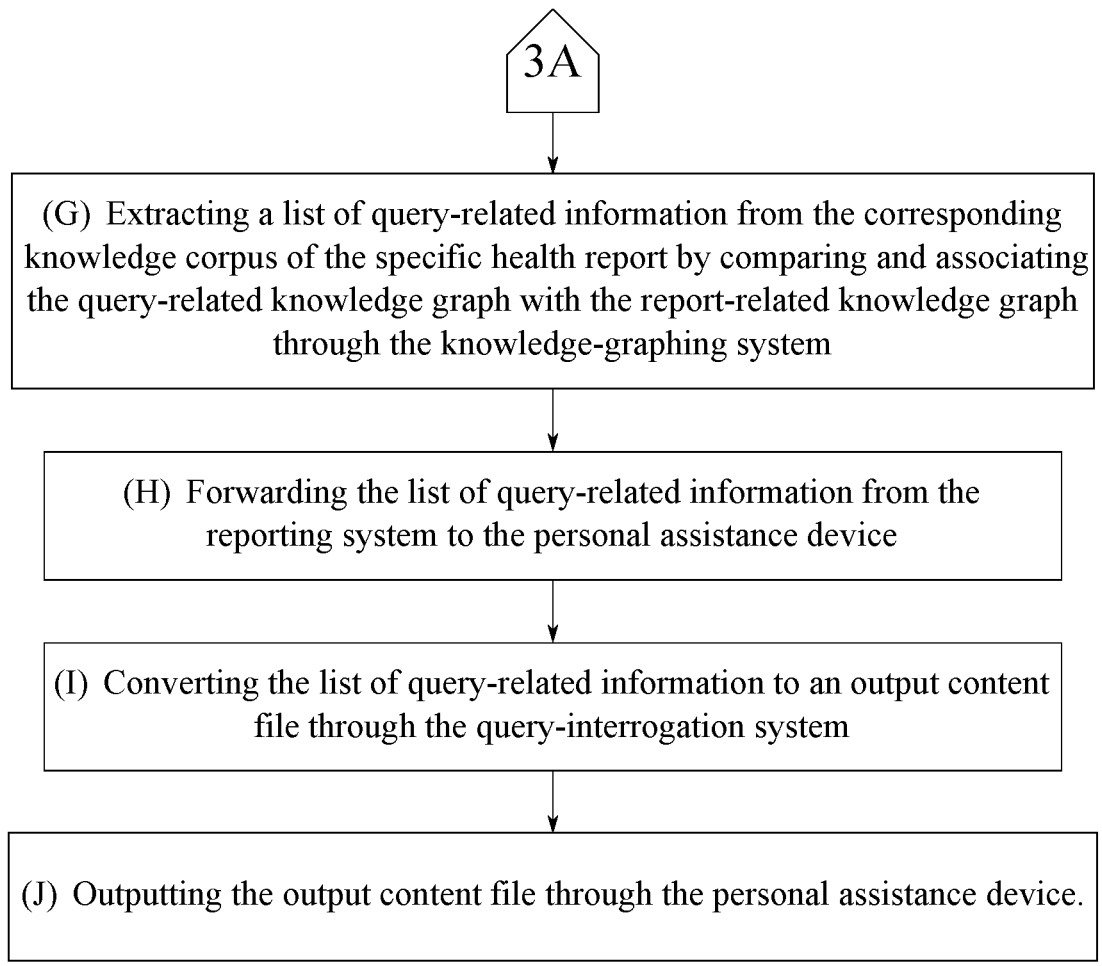
FIG. 3B is a continuation thereof, further illustrating the basic overall process of the present invention.
Figure 4:
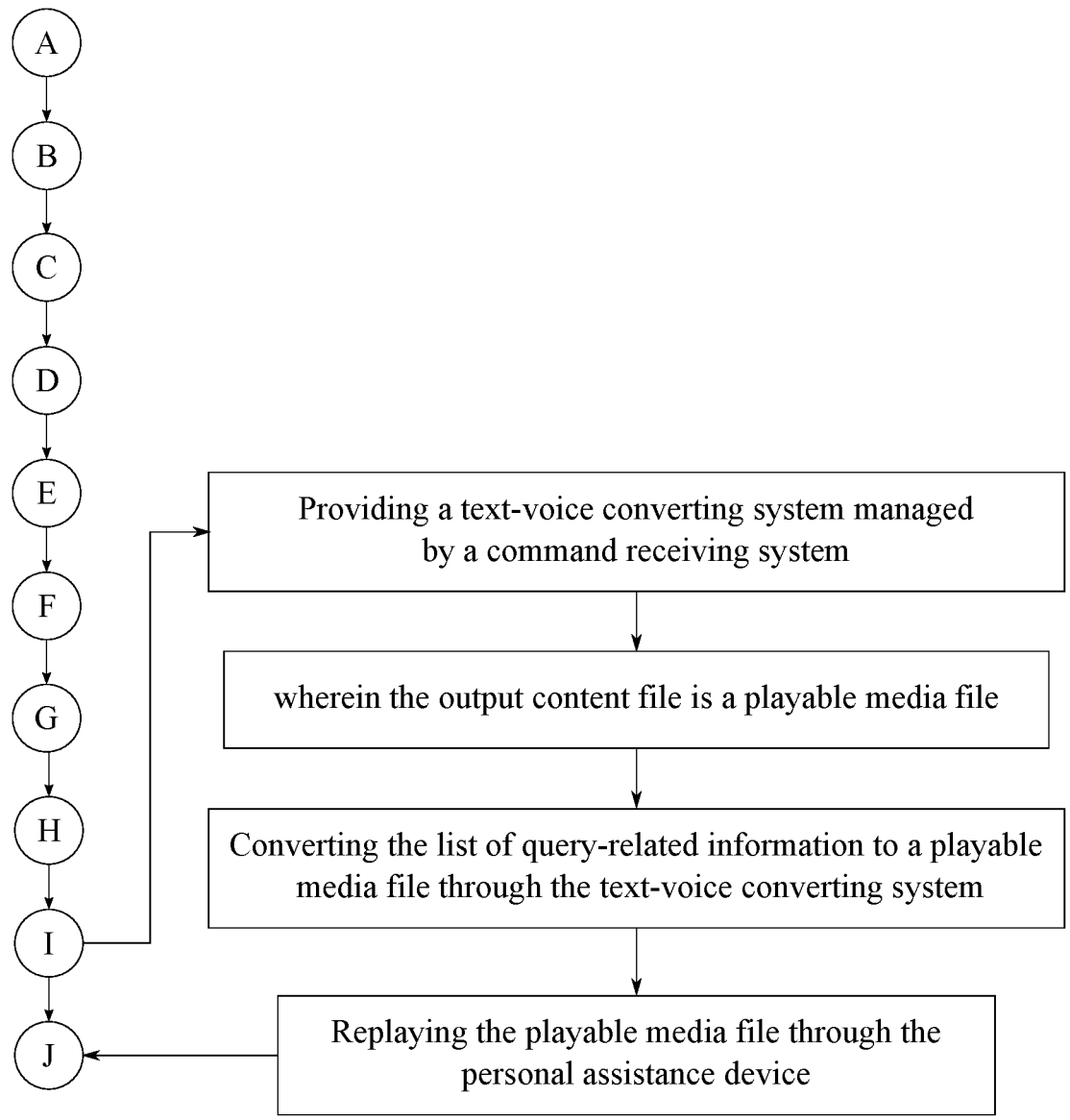
FIG. 4 is a flowchart illustrating the basic overall process of utilizing a text-voice converting system.
Figure 5:
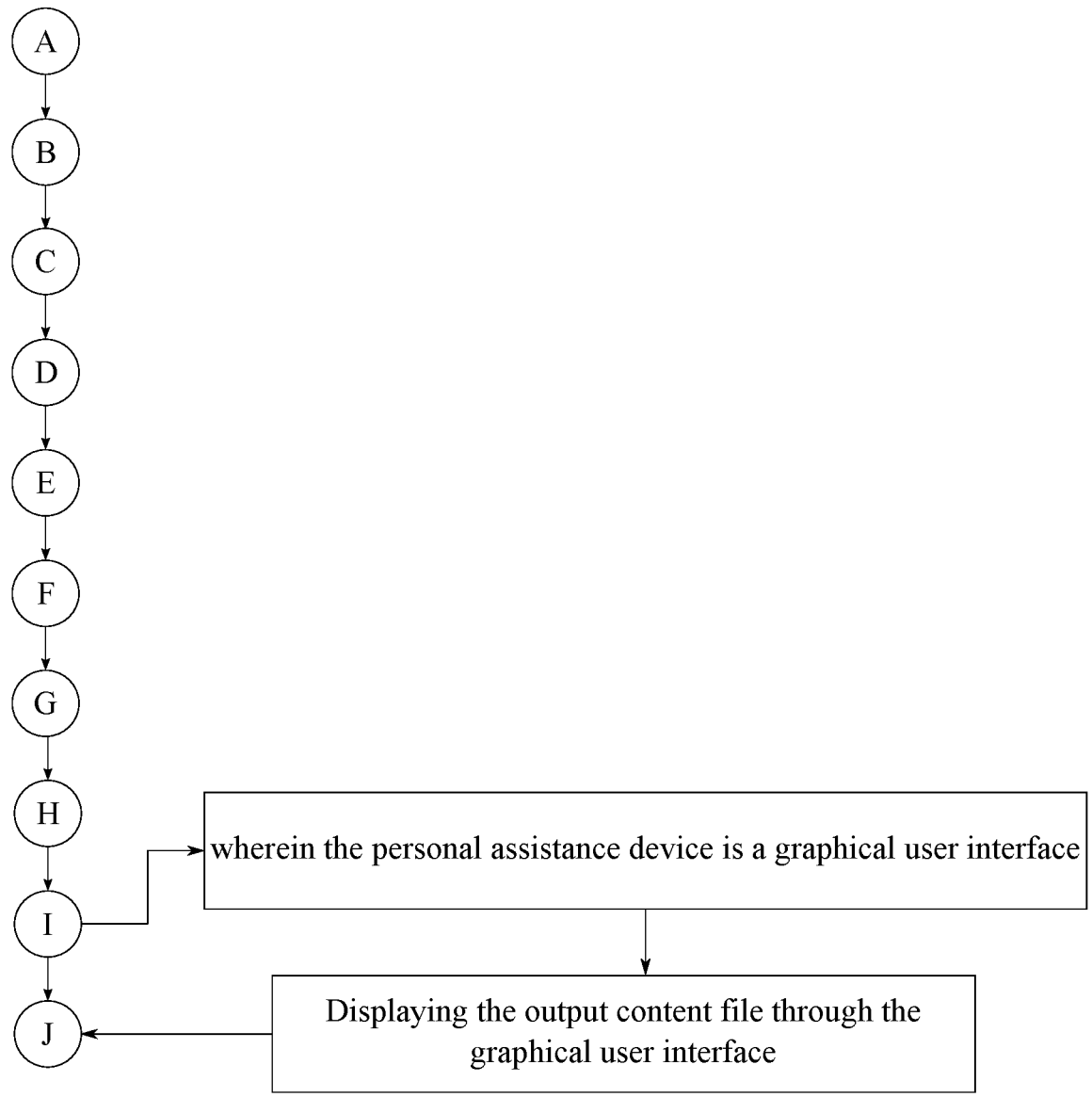
FIG. 5 is a flowchart illustrating the basic overall process of utilizing a graphical user interface.

As illustrated in FIG. 5, if the personal assistance device is a graphical user interface in another embodiment of the present invention, the output content file will be displayed through the graphical user interface. The graphical user interface will display the output content file and guide the user through the interrogation process by displaying contextually relevant prompts generated via a plurality of artificial intelligence (AI) modules embedded in the query-interrogation system. The graphical user interface can be, but is not limited to, a mobile phone or a computer.

Figure 6:
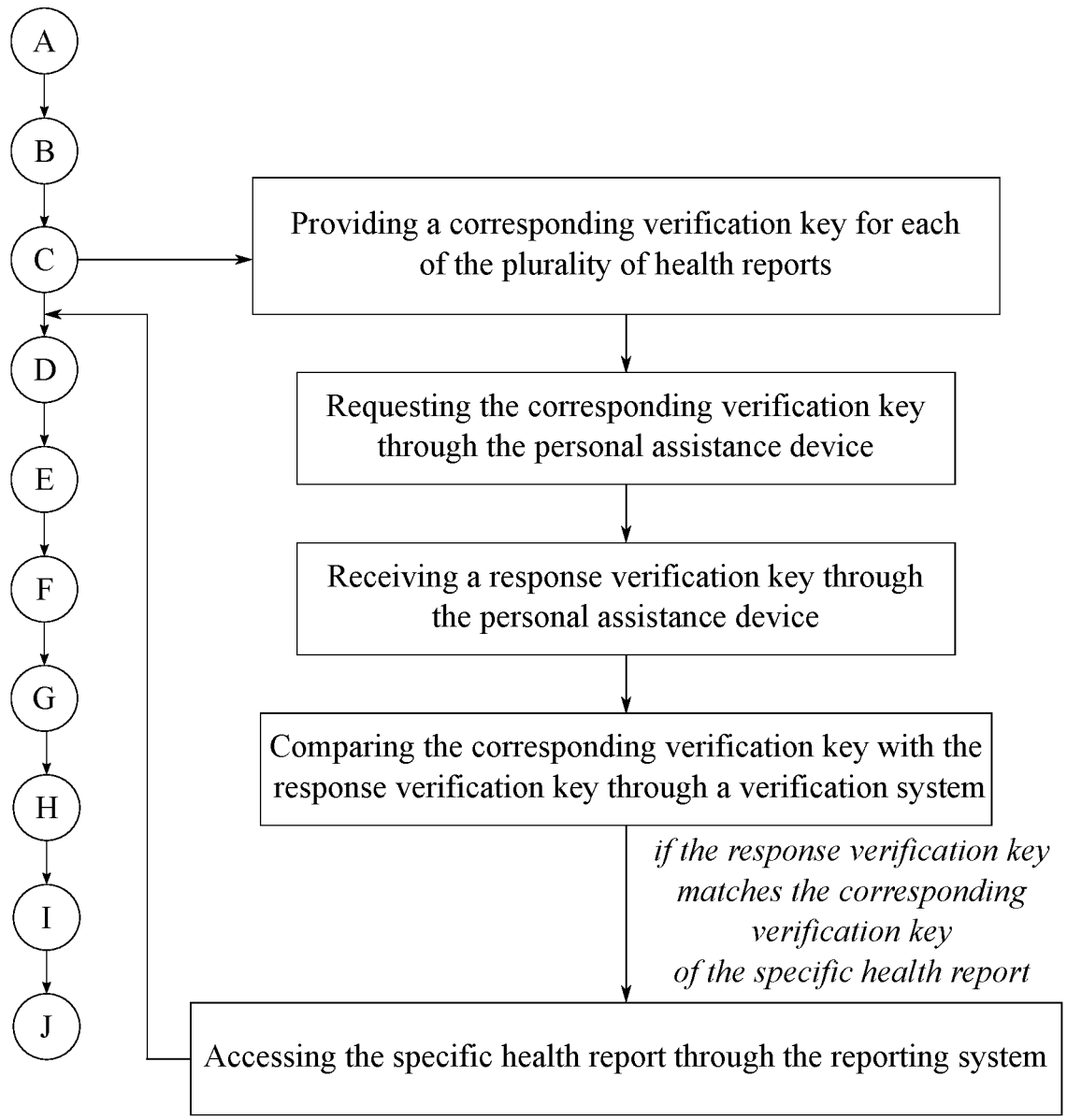
FIG. 6 is a flowchart illustrating the basic overall process of the verification system of the present invention.

As seen in FIG. 6, in order to provide security to the plurality of health reports, the present invention executes a verification process prior to providing a response to the health report-related query. To do so, the present invention is initially provided with a corresponding verification key for each of the plurality of health reports. Thus, a health report selected from the plurality of health reports can only be accessed after the corresponding verification key is provided. In the process of verifying the user who is requesting access to the specific health report, the present invention requests the corresponding verification key through the personal assistance device. When the user provides a response verification key, the present invention receives a response verification key through the personal assistance device. To ensure that the response verification key matches the corresponding verification key, the present invention compares the response verification key with the corresponding verification key through a verification system that is preferably managed by the at least one remote server. When the comparison is complete and if the response verification key matches the corresponding verification key of the specific health report, the present invention grants access to the specific health report through the reporting system.

Figure 7:
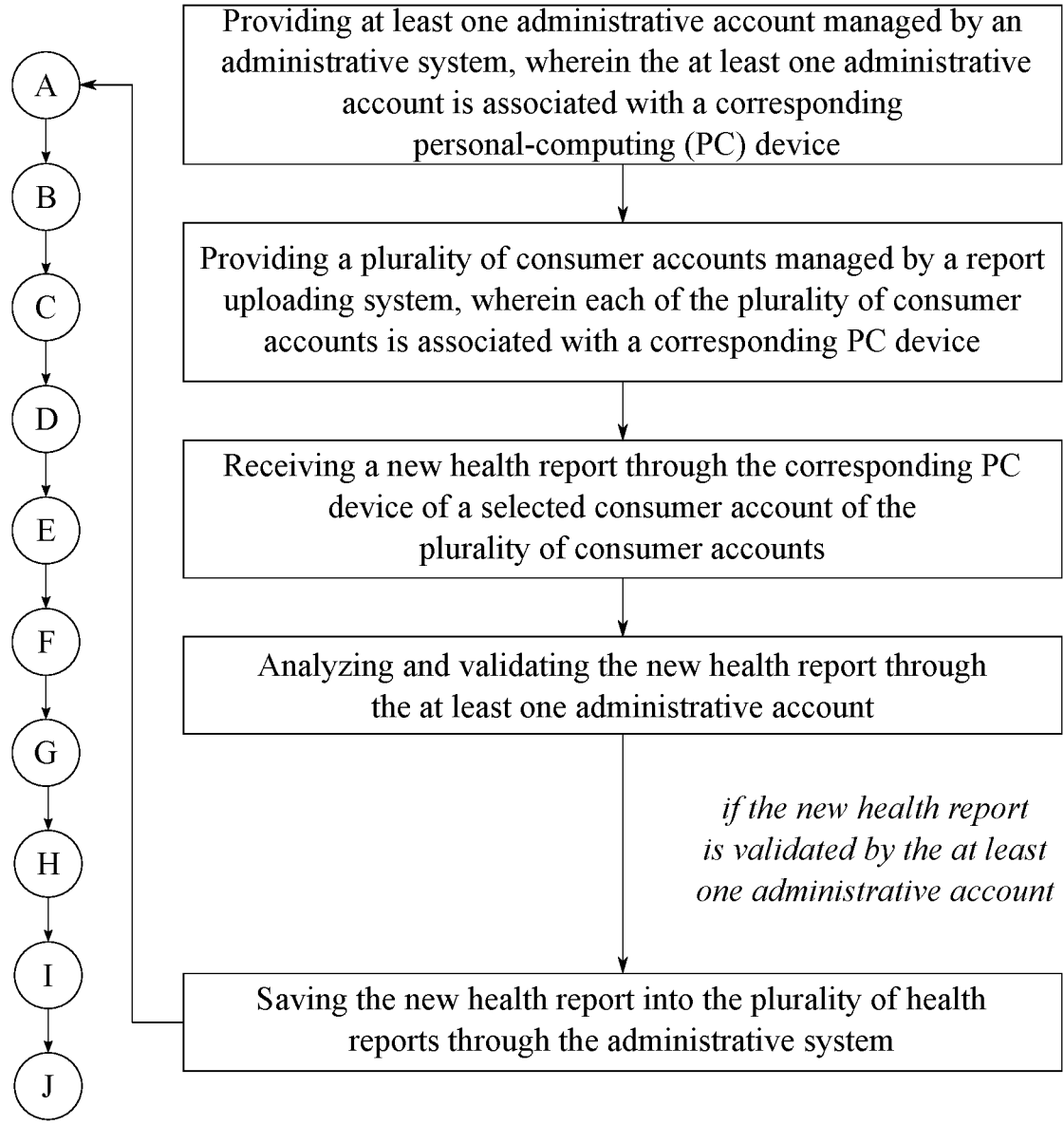
FIG. 7 is a flowchart illustrating the basic overall process of the administrative system of the present invention.

As seen in FIG. 7, the present invention is provided with at least one administrative account that is managed by an administrative system which is preferably managed by the at least one remote server. The present invention is also provided with a plurality of consumer accounts that is managed by a report uploading system which is preferably managed by the at least one remote server. Each of the plurality of consumer accounts has the ability to upload a new health report into the plurality of health reports. The at least one administrative account is utilized to validate the new health report uploaded by a selected account of the plurality of consumer accounts. To facilitate the uploading process and the validating process, both the plurality of consumer accounts and the at least one administrative account is associated with a corresponding personal computing (PC) device. The corresponding PC device can be, but is not limited to, a mobile phone and a computer.

When a new health report needs to be uploaded, the present invention receives the new health report through the corresponding PC device of the selected consumer account of the plurality of consumer accounts. When received, the at least one administrative account analyzes and validates the new health report through the corresponding PC device of the at least one administrative account. To ensure the accuracy of the validation process, the at least one administrative account is preferably operated by a certified counselor in the healthcare field. However, the at least one administrative account can be programmed to be operated by a health report-validation system that is managed by the administrative system. The need to manually validate the new health report is eliminated with the use of the health report-validation system. If the new health report is validated through the at least one administrative account, the present invention proceeds to save the new health report into the plurality of health reports via the administrative system.

Figure 8:
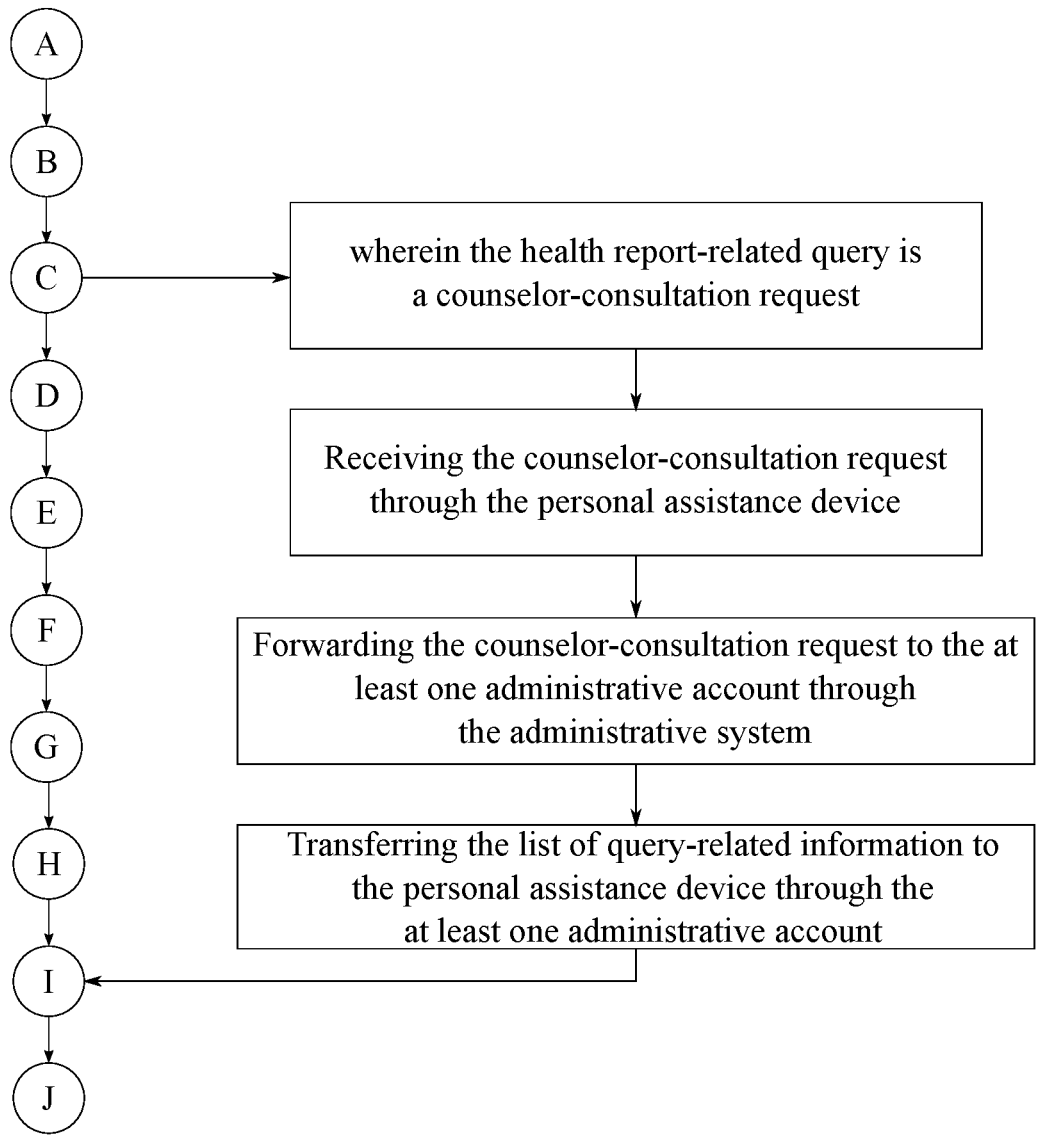
FIG. 8 is a flowchart illustrating the basic overall process, wherein the health report-related query is a counselor-consultation request.

As seen in FIG. 8, the present invention also allows the user to directly contact a certified counselor in order to get the list of query-related information. In such instances, the health report-related query will be a counselor-consultation request. When the counselor-consultation request is received through the personal assistance device, the present invention forwards the counselor-consultation request to the at least one administrative account through the administrative system. Thus, a certified counselor or other comparable healthcare professional can interact with the user by transferring the list of query-related information to the personal assistance device through the at least one administrative account.

Although the invention has been explained in relation to its preferred embodiment, it is to be understood that many other possible modifications and variations can be made without departing from the spirit and scope of the invention as hereinafter claimed.

What is claimed is:

1. A method of retrieving information from a health report through a machine assisted interrogation process comprises the steps of:
   (A) providing a personal assistance device, wherein the personal assistance device is communicably coupled with a reporting system;
   (B) providing a reporting system, wherein the reporting system comprises a plurality of health reports and a query-interrogation system;
   (C) receiving a health report-related query through the personal assistance device, wherein the health report-related query corresponds to a specific health report from the plurality of health reports;
   (D) forwarding the health report-related query to the reporting system through the personal assistance device;
   (E) selecting the specific health report from the plurality of health reports through the query-interrogation system;
   (F) compiling a corresponding knowledge corpus for the specific health report through a knowledge-graphing system, wherein the corresponding knowledge corpus includes a query-related knowledge graph and a report-related knowledge graph;
   (G) extracting a list of query-related information from the corresponding knowledge corpus of the specific health report by comparing and associating the query-related knowledge graph with the report-related knowledge graph through the knowledge-graphing system;
   (H) forwarding the list of query-related information from the reporting system to the personal assistance device;
   (I) converting the list of query-related information to an output content file through the query-interrogation system; and
   (J) outputting the output content file through the personal assistance device.

2. The method of retrieving information from a health report through a machine assisted interrogation process as claimed in claim 1 further comprises the steps of:

providing a text-voice converting system managed by a command receiving system;

wherein the output content file is a playable media file;

converting the list of query-related information to a playable media file through the text-voice converting system; and replaying the playable media file through the personal assistance device.

3. The method of retrieving information from a health report through a machine assisted interrogation process as claimed in claim 1 further comprises the steps of:

wherein the personal assistance device is a graphical user interface; and displaying the output content file through the graphical user interface.

4. The method of retrieving information from a health report through a machine assisted interrogation process as claimed in claim 1 further comprises the steps of:

providing a corresponding verification key for each of the plurality of health reports;

requesting the corresponding verification key through the personal assistance device;

receiving a response verification key through the personal assistance device;

comparing the corresponding verification key with the response verification key through a verification system; and accessing the specific health report through the reporting system, if the response verification key matches the corresponding verification key of the specific health report.

5. The method of retrieving information from a health report through a machine assisted interrogation process as claimed in claim 1 further comprises the steps of:

providing at least one administrative account managed by an administrative system, wherein the at least one administrative account is associated with a corresponding personal-computing (PC) device;

providing a plurality of consumer accounts managed by a report uploading system, wherein each of the plurality of consumer accounts is associated with a corresponding PC device;

receiving a new health report through the corresponding PC device of a selected consumer account of the plurality of consumer accounts;

analyzing and validating the new health report through at least one administrative account; and saving the new health report into the plurality of health reports through the administrative system, if the new health report is validated by the at least one administrative account.

6. The method of retrieving information from a health report through a machine assisted interrogation process as claimed in claim 5, wherein the at least one administrative account is operated by a health report-validation system managed by the administrative system.

7. The method of retrieving information from a health report through a machine assisted interrogation process as claimed in claim 5 further comprises the steps of:

wherein the health report-related query is a counselor-consultation request;

receiving the counselor-consultation request through the personal assistance device;

forwarding the counselor-consultation request to the at least one administrative account through the administrative system; and transferring the list of query-related information to the personal assistance device through the at least one administrative account.

8. The method of retrieving information from a health report through a machine assisted interrogation process as claimed in claim 1 further comprises the steps of:

scanning the specific health report and identifying a first list of relevant information via the knowledge-graphing system;

generating a plurality of report-related expressions with the first list of relevant information, wherein the plurality of report-related expressions is generated through the query-interrogation system; and saving the plurality of report-related expressions into the report-related knowledge graph through the query-interrogation system.

9. The method of retrieving information from a health report through a machine assisted interrogation process as claimed in claim 1 further comprises the steps of:

providing an external library for each of the plurality of health reports, wherein the external library communicably linked with the report-related knowledge graph and is managed by a content-updating system;

providing a plurality of external database plugins managed by the content updating system;

receiving a plurality of health report-related information from each of the plurality of external database plugins; and saving the plurality of health-report related information into the external library through the query-interrogation system.

10. The method of retrieving information from a health report through a machine assisted interrogation process as claimed in claim 8, wherein the first list of relevant information comprises a plurality of healthcare-related ontologies.

11. The method of retrieving information from a health report through a machine assisted interrogation process as claimed in claim 8, wherein the first list of relevant information comprises a plurality of healthcare-related keywords.

12. The method of retrieving information from a health report through a machine assisted interrogation process as claimed in claim 1 further comprises the steps of:

providing a natural language-understanding system;

monitoring the health-report related query and identifying a second list of relevant information via the query-interrogation system;

generating a plurality of query-related expressions with the second list of relevant information, wherein the plurality of query-related expressions is generated through the natural language-understanding system; and saving the plurality of query-related expressions into the query-related knowledge graph through the query-interrogation system.

13. The method of retrieving information from a health report through a machine assisted interrogation process as claimed in claim 12 further comprises the steps of:

providing a self-learning system;

comparing the second list of relevant information with a plurality of data-fields on the corresponding knowledge corpus through the machine-learning module; and updating the plurality of data-fields with the second list of relevant information, if the second list of relevant information is not present in the plurality of data-fields.

14. The method of retrieving information from a health report through a machine assisted interrogation process as claimed in claim 12, wherein the second list of relevant information comprises a plurality of healthcare-related ontologies.

15. The method of retrieving information from a health report through a machine assisted interrogation process as claimed in claim 12, wherein the second list of relevant information comprises a plurality of healthcare-related keywords.

\* \* \* \* \*